US012734361B2

(12) United States Patent
Dinsmoor et al.

(10) Patent No.: US 12,734,361 B2
(45) Date of Patent: Sep. 15, 2026

(54) PHASE ALIGNMENT OF ECAPS

(71) Applicant: Medtronic, Inc., Minneapolis, MN (US)

(72) Inventors: David A. Dinsmoor, North Oaks, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 284 days.

(21) Appl. No.: 17/409,484

(22) Filed: Aug. 23, 2021

(65) Prior Publication Data

US 2022/0062638 A1 Mar. 3, 2022

Related U.S. Application Data

(60) Provisional application No. 63/073,673, filed on Sep. 2, 2020.

(51) Int. Cl.
*A61N 1/36* (2006.01)
*A61N 1/05* (2006.01)

(52) U.S. Cl.
CPC ....... *A61N 1/36135* (2013.01); *A61N 1/0534* (2013.01); *A61N 1/0551* (2013.01)

(58) Field of Classification Search
CPC .............. A61N 1/36135; A61N 1/0534; A61N 1/0551; A61N 1/36139; A61N 1/36067
See application file for complete search history.

(56) References Cited

U.S. PATENT DOCUMENTS 5,603,726 A 2/1997 Schulman et al.
5,800,465 A 9/1998 Thompson et al.
6,157,861 A 12/2000 Faltys et al.
(Continued)

FOREIGN PATENT DOCUMENTS

EP 2396072 B1 3/2013
EP 3013413 A1 5/2016
(Continued)

OTHER PUBLICATIONS

International Search Report and Written Opinion of International Application No. PCT/US2021/047341, dated Jan. 5, 2022, 10 pp.
(Continued)

*Primary Examiner* — Allen Porter
(74) *Attorney, Agent, or Firm* — Shumaker & Sieffert, P.A.

(57) ABSTRACT

Systems, devices, methods, and techniques are described for phase misalignment correction for evoked compound action potential (ECAP) measurement from alternating polarity stimulation. An example system includes processing circuitry that receives a first ECAP signal elicited by a first polarity configuration of stimulus electrodes and receives a second ECAP signal elicited by a second polarity configuration of the stimulus electrodes opposite the first polarity configuration. The processing circuitry also generates an adjusted second ECAP signal by temporally aligning at least a portion of the second ECAP signal to at least a portion of the first ECAP signal, and generates a composite ECAP signal based on the first ECAP signal and the adjusted second ECAP signal. Additionally, the processing circuitry outputs the composite ECAP signal.

20 Claims, 8 Drawing Sheets

(56) References Cited

U.S. PATENT DOCUMENTS 6,205,360 B1 3/2001 Carter
6,289,247 B1 9/2001 Faltys et al.
6,314,325 B1 11/2001 Fitz
6,421,566 B1 7/2002 Holsheimer
6,505,078 B1 1/2003 King et al.
6,675,046 B2 1/2004 Holsheimer
6,850,802 B2 2/2005 Holsheimer
6,988,006 B2 1/2006 King et al.
7,076,292 B2 7/2006 Forsberg
7,206,640 B1 4/2007 Overstreet
7,333,858 B2 2/2008 Killian et al.
7,577,480 B2 8/2009 Zeijlemaker
7,616,999 B2 11/2009 Overstreet et al.
7,657,318 B2 2/2010 King et al.
7,689,289 B2 3/2010 King
7,742,810 B2 6/2010 Moffitt et al.
7,792,583 B2 9/2010 Miesel et al.
8,036,747 B2 10/2011 Thacker et al.
8,090,446 B2 1/2012 Fowler et al.
8,504,150 B2 8/2013 Skelton
8,620,441 B2 12/2013 Greenberg et al.
8,676,329 B2 3/2014 Wacnik et al.
8,694,108 B2 4/2014 Alataris et al.
8,708,934 B2 4/2014 Skelton et al.
8,712,533 B2 4/2014 Alataris et al.
8,712,534 B2 4/2014 Wei
8,751,009 B2 6/2014 Wacnik
8,897,888 B2 11/2014 Parker et al.
8,923,984 B2 12/2014 Parker et al.
9,002,460 B2 4/2015 Parker
9,072,910 B2 7/2015 Parker et al.
9,089,714 B2 7/2015 Robinson
9,089,715 B2 7/2015 Parker et al.
9,138,582 B2 9/2015 Doan et al.
9,155,892 B2 10/2015 Parker et al.
9,283,373 B2 3/2016 Parker et al.
9,302,112 B2 4/2016 Bornzin et al.
9,339,655 B2 5/2016 Carbunaru
9,364,667 B1 6/2016 Dinsmoor et al.
9,381,356 B2 7/2016 Parker et al.
9,386,934 B2 7/2016 Parker et al.
9,387,325 B1 7/2016 Min et al.
9,566,439 B2 2/2017 Single et al.
9,597,507 B2 3/2017 Johanek et al.
9,700,713 B2 7/2017 Robinson et al.
9,872,990 B2 1/2018 Parker et al.
9,993,646 B2 6/2018 Parramon et al.
10,183,168 B2 1/2019 Baru et al.
10,569,088 B2 2/2020 Dinsmoor et al.
10,933,242 B2 3/2021 Torgerson
2003/0204214 A1* 10/2003 Ferek-Patric .......... A61N 1/371 607/27
2004/0267333 A1 12/2004 Kronberg
2008/0221640 A1 9/2008 Overstreet et al.
2008/0300655 A1* 12/2008 Cholette ............ A61N 1/36135 607/60
2011/0054570 A1 3/2011 Lane
2011/0071589 A1 3/2011 Starkebaum et al.
2011/0077712 A1 3/2011 Killian
2011/0125223 A1 5/2011 Carbunaru et al.
2012/0155188 A1 6/2012 Buettner et al.
2012/0191157 A1* 7/2012 Stypulkowski ...... A61N 1/0534 607/45
2013/0208390 A1 8/2013 Singh et al.
2013/0268021 A1 10/2013 Moffitt
2013/0289664 A1 10/2013 Johanek
2013/0289683 A1 10/2013 Parker et al.
2014/0005753 A1 1/2014 Carbunaru
2014/0025146 A1 1/2014 Alataris et al.
2014/0031896 A1 1/2014 Alataris et al.
2014/0031905 A1 1/2014 Irazoqui et al.
2014/0074189 A1 3/2014 Moffitt
2014/0142656 A1 5/2014 Alataris et al.
2014/0142673 A1 5/2014 Alataris et al.
2014/0194772 A1 7/2014 Single et al.
2014/0236042 A1 8/2014 Parker et al.
2014/0236257 A1 8/2014 Parker et al.
2014/0243924 A1 8/2014 Zhu et al.
2014/0243926 A1 8/2014 Carcieri et al.
2014/0243931 A1 8/2014 Parker et al.
2014/0277282 A1 9/2014 Jaax
2014/0288577 A1 9/2014 Robinson et al.
2014/0293737 A1 10/2014 Parker et al.
2014/0296737 A1* 10/2014 Parker .................. A61B 5/4836 600/554
2014/0296936 A1 10/2014 Alataris et al.
2014/0324143 A1 10/2014 Robinson et al.
2014/0371813 A1 12/2014 King et al.
2014/0378941 A1 12/2014 Su et al.
2014/0379043 A1 12/2014 Howard
2015/0005842 A1 1/2015 Lee et al.
2015/0012068 A1 1/2015 Bradley et al.
2015/0032181 A1 1/2015 Baynham et al.
2015/0057729 A1 2/2015 Parker et al.
2015/0127062 A1 5/2015 Holley et al.
2015/0179177 A1 6/2015 Nagao
2015/0282725 A1 10/2015 Single
2015/0313487 A1 11/2015 Single et al.
2015/0360031 A1 12/2015 Bornzin et al.
2015/0374999 A1 12/2015 Parker et al.
2016/0082252 A1 3/2016 Hershey et al.
2016/0121124 A1 5/2016 Johanek et al.
2016/0129272 A1 5/2016 Hou et al.
2016/0136420 A1 5/2016 Brink et al.
2016/0157769 A1* 6/2016 Min ..................... A61B 5/0536 600/547
2016/0158550 A1 6/2016 Hou et al.
2016/0166164 A1 6/2016 Obradovic et al.
2016/0175594 A1 6/2016 Min et al.
2016/0206883 A1 7/2016 Bomzin et al.
2016/0287126 A1 10/2016 Parker et al.
2016/0287182 A1 10/2016 Single
2016/0346534 A1 12/2016 Isaacson et al.
2016/0361542 A1 12/2016 Kaula et al.
2017/0001017 A9 1/2017 Parker et al.
2017/0049345 A1 2/2017 Single
2017/0071490 A1 3/2017 Parker et al.
2017/0135624 A1 5/2017 Parker
2017/0173332 A1 6/2017 Overstreet
2017/0209695 A1 7/2017 Solomon
2017/0216587 A1 8/2017 Parker
2017/0216602 A1 8/2017 Waataja et al.
2017/0296823 A1 10/2017 Hershey et al.
2017/0361101 A1 12/2017 Single
2017/0361103 A1 12/2017 Hadjiyski
2018/0056073 A1 3/2018 Torgerson
2018/0078769 A1 3/2018 Dinsmoor et al.
2018/0110987 A1 4/2018 Parker
2018/0117335 A1 5/2018 Parker et al.
2018/0126169 A1 5/2018 Hou et al.
2018/0132760 A1 5/2018 Parker
2019/0099601 A1 4/2019 Torgerson
2019/0105496 A1 4/2019 Min et al.
2019/0175904 A1* 6/2019 Baru .................... A61N 1/0551
2019/0209844 A1 7/2019 Esteller et al.
2019/0366094 A1* 12/2019 Esteller ................ A61B 5/7217
2019/0388692 A1* 12/2019 Dinsmoor .......... A61N 1/36067
2019/0388695 A1 12/2019 Dinsmoor et al.
2020/0171312 A1 6/2020 Dinsmoor et al.
2020/0171313 A1 6/2020 Dinsmoor et al.
2021/0101007 A1 4/2021 Hamner et al.
2021/0121698 A1 4/2021 Dinsmoor et al.
2021/0121700 A1 4/2021 Dinsmoor et al.
2022/0007987 A1* 1/2022 Huang ................. A61B 5/4041

FOREIGN PATENT DOCUMENTS

EP 3024540 B1 10/2018
WO 2002009808 A1 2/2002
WO 2010058178 A1 5/2010
WO 2012155188 A1 11/2012
WO 2013116161 A1 8/2013
WO 2014210373 A1 12/2014
WO 2015070281 A1 5/2015

(56) References Cited

FOREIGN PATENT DOCUMENTS

| | | | |
|---|---|---|---|
| WO | 2015143509 | A1 | 10/2015 |
| WO | 2015179177 | A1 | 11/2015 |
| WO | 2015179281 | A2 | 11/2015 |
| WO | 2016090420 | A1 | 6/2016 |
| WO | 2016090436 | A1 | 6/2016 |
| WO | 2016191808 | A1 | 12/2016 |
| WO | 2017100866 | A1 | 6/2017 |
| WO | 2017106503 | A1 | 6/2017 |
| WO | 2017173493 | A1 | 10/2017 |
| WO | 2017184238 | A1 | 10/2017 |
| WO | 2017219096 | A1 | 12/2017 |
| WO | 2018/080754 | A1 | 5/2018 |
| WO | 2018080753 | A1 | 5/2018 |
| WO | 2018106813 | A1 | 6/2018 |
| WO | 2019231794 | A1 | 12/2019 |

OTHER PUBLICATIONS

"St. Jude's Prodigy Neurostimulator with Burst Technology," Medgadget, http://www.medgadget.com, Mar. 20, 2014, 4 pp.

Abejon et al., "Back pain coverage with spinal cord stimulation: A different treatment for each patient," International Neuromodulation Society, Jun. 10, 2015; 567, Abstract Only, 1 pp.

Abeloos MD "High density stimulation as an alternative to uncomfortable cervical tonic spinal cord stimulation: case report," International Neuromodulation Society 12th World Congress, Jun. 11-15, 2015, Abstract Only, 1 pp.

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Crosby et al., "Modulation of activity and conduction in single dorsal column axons by kilohertz-frequency spinal cord stimulation," American Physiological Society, published online Oct. 19, 2016, 27 pp.

Cuellar et al., "Effect of High-Frequency Alternating Current on Spinal Afferent Nociceptive Transmission," Neuromodulation: Technology at the Neural Interface, vol. 16, No. 4, DOI: 10.1111/ner.12015, Nov. 6, 2012, pp. 318-327.

Cui et al., "Effect of spinal cord stimulation on tactile hypersensitivity in mononeuropathic rats is potentiated by simultaneous GABA. sub B. and adenosine receptor activation," Elsevier, Neuroscience Letters, vol. 247, Apr. 1998, pp. 183-186.

Cui et al., "Spinal cord stimulation attenuates augmented dorsal horn release of excitatory amino acids in mononeuropathy via a GABAergic mechanism," International Association for the STudy of Pain, Pain, vol. 73, Oct. 1997, pp. 87-95.

De Ridder et al., "Burst spinal cord stimulation for limb and back pain," Science Direct, World Neurosurgery, vol. 80, No. 5, http://dx.doi.org/10.1016/j.wneu.2013.01.040, Nov. 2013, pp. 642-649, e641.

De Ridder et al., "Burst Spinal Cord Stimulation: Toward Paresthesia-Free Pain Suppression," Neurosurgery, vol. 66, No. 5, May 2010, pp. 986-990.

Downey, "Asynchronous Neuromuscular Electrical Stimulation," University of Florida, 2015, accessed on Jul. 18, 2016, 107 pp.

Duyvendak et al., "High density stimulation: a novel programming paradigm for the treatment of chronic back and leg pain," Abstracts, International Neuromodulation Society 12th World Congress, Neuromodulation, vol. 18, Jun. 11-15, 2015, 1 pp.

Gao et al., "Effects of spinal cord stimulation with "standard clinical" and higher frequencies on peripheral blood flow in rats," Elsevier, Brain Research, vol. 1313, doi:10.1016/j.brainres.2009.11.072, available online Dec. 3, 2009, pp. 53-61.

Grider et al., "High Frequency (1000 Hz) Stimulation Using Commercially Available Implantable Pulse Generator," North American Neuromodulation Society, No. 198, Dec. 2013, Abstract Only, 2 pp.

Guan et al., "Spinal Cord Stimulation-induced Analgesia: Electrical Stimulation of Dorsal Column and Dorsal Roots Attenuates Dorsal Horn Neuronal Excitability in Neuropathic Rats," The American Society of Anesthesiologists, Inc., Anesthesiology, vol. 113, No. 6, Dec. 2010, pp. 1392-1405.

Guan, "Spinal Cord Stimulation: Neurophysiological and Neurochemical Mechanisms of Action" Current Pain and Headache Reports, Vo. 16, DOI 10.1007s11916-014-0260-4, Mar. 8, 2012, pp. 217-225.

Holsheimer, "Computer modelling of spinal cord stimulation and its contribution to therapeutic efficacy," International Medical Society of Paraplegia, Spinal Cord, vol. 36, Aug. 1998, pp. 531-540.

Hubscher et al., "Convergence and cross talk in urogenital neural circuitries," The American Physiological Society, Journal of Neurophysiology, vol. 110, doi:10.1152/jn.00297.2013, Aug. 7, 2013, pp. 1997-2005.

Hunt et al. "The Molecular Dynamics of Pain Control," MacMillan Magazines, Ltd., Nature Reviews, Neuroscience, vol. 2, No. 2, Feb. 2001, pp. 83-91.

Kemler et al., "Spinal Cord Stimulation in Patients with Chronic Reflex Sympathetic Dystrophy," The New England Journal of Medicine, vol. 343, No. 9, Aug. 31, 2000, pp. 618-624.

Kilgore et al., "Reversible Nerve Conduction Block Using Kilohertz Frequency Alternating Current," International Modulation Society, Neuromodulation, vol. 17, DOI: 10.1111/ner.12100, Aug. 2013, pp. 242-255.

Kumar et al., "Spinal cord stimulation versus conventional medical management for neuropathic pain: a multicentre randomised controlled trial in patients with failed back surgery syndrome," International Association for the Study of Pain, Pain, vol. 132, No. 102, Jul. 2007, pp. 179-188.

Likar et al., "High density spinal cord stimulation: a multi-center experience," Abstracts, International Neuromodulation Society 12th World Congress, Neuromodulation, vol. 18, Jun. 11-15, 2015, 1 pp.

Maeda et al., "Increased c-fos immunoreactivity in the spinal cord and brain following spinal cord stimulation is frequency-dependent," Elsevier, Brain Research, vol. 1259, Mar. 9, 2009, pp. 40-50.

Maeda et al., "Low frequencies, but not high frequencies of bi-polar spinal cord stimulation reduce cutaneous and muscle hyperalgesia induced by nerve injury," International Association for the Study of Pain, Pain. vol. 138, No. 1, Feb. 2008, pp. 143-152.

Maggi et al., "Effect of urethane anesthesia on the micturition reflex in capsaicin-treated rats," Elsevier, Journal of the Autonomic Nervous System, vol. 30, No. 3, Jan. 1990, pp. 247-251.

North et al., "Clinical outcomes of 1 kHz subperception spinal cord stimulation (SCS): Results of a prospective randomized controlled crossover trial," Abstracts, International Neuromodulation Society, Neuromodulation, vol. 18, Jun. 2015, 1 pp.

North et al., "Spinal Cord Stimulation versus Repeated Lumbosacral Spine Surgery for Chronic Pain: A Randomized, Controlled Trail," Neurosurgery, vol. 56, No. 1, Jan. 2005, pp. 98-106; discussion 106-107.

Ranck, Jr. et al., "Which Elements are Excited in Electrical Stimulation of Mammalian Central Nervous System: A Review," Elsevier Scientific Publishing Company, Brain Research, vol. 98, No. 3, Nov. 21, 1975, pp. 417-440.

Replogle MD et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato et al., "Spinal cord stimulation reduces hypersensitivity through activation of opioid receptors in a frequency-dependent manner," European Journal of Pain, vol. 4, Apr. 2013, pp. 551-561.

Schu et al., "A Prospective, Randomised, Double-blind, Placebo-controlled Study to Examine the Effectiveness of Burst Spinal Cord Stimulation Patterns for the Treatment of Failed Back Surgery Syndrome," International Neuromodulation Society, Neuromodulation, vol. 17, No. 5, Apr. 2014, pp. 443-450.

Shechter et al., "Conventional and Kilohertz-frequency Spinal Cord Stimulation Produces Intensity- and Frequency-dependent Inhibi-

(56) References Cited

OTHER PUBLICATIONS tion of Mechanical Hypersensitivity in a Rat Model of Neuropathic Pain," Anesthesiology, vol. 119, No. 2, Aug. 2013, pp. 422-432.
Sluka, et al., "High-frequency, but not low-frequency, transcutaneous electrical nerve stimulation reduces aspartate and glutamate release in the spinal cord dorsal horn," Journal of Neurochemistry, vol. 95, No. 6, Oct. 17, 2005, pp. 1794-1801.
Smith et al., "Successful Use of High-Frequency Spinal Cord Stimulation Following Traditional Treatment Failure," Stereotactic and Functional Neurosurgery, vol. 93, No. 3, Apr. 1, 2015, pp. 190-193.
Snellings et al., "Effects of stimulation site and stimulation parameters on bladder inhibition by electrical nerve stimulation," BJU International, Jul. 2012, pp. 136-143.
Song et al., "Efficacy of Kilohertz-Frequency and Conventional Spinal Cord Stimulation in Ray Models of Different Pain Conditions," International Neuromodulation Society, Neuromodulation, vol. 17, No. 3, Jan. 2014, pp. 226-234.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.
Walter et al., "Inhibiting the Hyperrflexic Bladder With Electrical Stimulation in a Spinal Animal Mode," Neurourology and Urodynamics, vol. 12, doi:10.1002/nau.1930120306, Oct. 19, 1992, pp. 241-253.
Wille et al., "Altering Conventional to High Density Spinal Cord Stimulation: An Energy Dose-Response Relationship In Neuropathic Pain Therapy," International Neuromodulation Society, Neuromodulation 2016, Aug. 2016, 9 pp.
Woock et al., "Activation and inhibition of the micturition reflex by penile afferents in the cat," The American Journal of Physiology—Regulatory, Integrative and Comparative Physiology, vol. 294, Apr. 23, 2008, pp. R1880-R1889.
Youn et al., The Effect of High-Frequency Stimulation on Sensory Thresholds in Chronic Pain Patients, Stereotact Funct Neurosurg, Oct. 8, 2015, pp. 355-359.
Mens., "Advances in Cochlear Implant Telemetry: Evoked Neural Responses, Electrical Field Imaging, and Technical Integrity," Sage Publications, vol. 11, No. 3, Sep. 2007, 17 pp.
Zeng et al., "Cochlear Implants: System Design, Integration and Evaluation," IEEE Rev Biomed Eng., Jan. 1, 2008, 66 pp.
International Preliminary Report on Patentability from International Application No. PCT/US2021/047341 dated Mar. 16, 2023, 7 pp.
First Examination Report from counterpart Australian Application No. 2021338199 dated Mar. 25, 2026, 3 pp.
First Office Action and Search Report, and translation thereof, from counterpart Chinese Application No. 202180054136.9 dated Jun. 24, 2026, 19 pp.

* cited by examiner

PHASE ALIGNMENT OF ECAPS

This application claims the benefit of U.S. Provisional Patent Application No. 63/073,673, filed Sep. 2, 2020, the entire contents of which is incorporated herein by reference.

TECHNICAL FIELD

This disclosure generally relates to medical devices, and more specifically, analyzing sensed electrical signals.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device.

SUMMARY

In general, systems, devices, and techniques are described for phase misalignment correction for evoked compound action potential (ECAP) measurement from alternating polarity stimulation. Alternating stimulation polarity for sensing ECAPs can be used to reduce the impact of stimulation artifacts and increase signal amplitude when sensing the ECAPs. Using a bi-polar electrode configuration, a system may sense a pair of ECAP signals using an alternating stimulus polarity for a combination of stimulus electrodes. The first polarity may include at least a first electrode as a cathode and at least a second electrode as an anode for a first stimulus, and the second opposite (or alternating) polarity may include at least a first electrode as the anode and at least a second electrode as the cathode. In this manner, the two delivered stimulus alternate polarities. A second set of electrodes is used to sense the resulting ECAPs signals from each respective stimulus polarity.

In systems where the stimulus electrodes and sensing electrodes are along the same axis or generally parallel axes, the timing of the first and second ECAP signals resulting from the respective stimulus polarities may be different due to, for example, the distance from the cathode to the sensing electrodes being different between the two opposite stimulus polarities (e.g., neural stimulation is generally initiated at the cathode). As described below, processing circuitry characterizes the phase misalignment between the two ECAP signals. For example, the processing circuitry may use the conduction velocity, the distance between the two electrodes, and/or the timing of a feature (such as, the first negative peak (N1) of the ECAP signal, etc.) on the first ECAP signal with respect to the corresponding feature of the second ECAP signal. The processing circuitry compensates for the misalignment by processing one or both ECAPs to adjust the timing characteristics such that the two ECAP signals are temporally aligned. The processing circuitry averages the two ECAP signals to generate a composite ECAP signal for further analysis, such as determining an effectiveness of stimulation, determining a placement a lead associated with the electrodes, migration of a lead associated with the electrodes, and/or posture of the patient, etc. The processing circuitry may be part of an implantable medical device (IMD), an external programmer, or a remote server (e.g., a cloud server, etc.).

An example system includes processing circuitry that receives a first ECAP signal elicited by a first polarity configuration of stimulus electrodes and receives a second ECAP signal elicited by a second polarity configuration of the stimulus electrodes opposite the first polarity configuration. The processing circuitry also generates an adjusted second ECAP signal by temporally aligning at least a portion of the second ECAP signal to at least a portion of the first ECAP signal, and generates a composite ECAP signal based on the first ECAP signal and the adjusted second ECAP signal. Additionally, the processing circuitry outputs at least a portion the composite ECAP signal.

An example method includes receiving a first ECAP signal elicited by a first polarity configuration of stimulus electrode, and receiving a second ECAP signal elicited by a second polarity configuration of the stimulus electrodes opposite the first polarity configuration. The method also includes generating an adjusted second ECAP signal by temporally aligning at least a portion of the second ECAP signal to at least a portion of the first ECAP signal, and generating a composite ECAP signal based on the first ECAP signal and the adjusted second ECAP signal. Additionally, the method includes outputting the composite ECAP signal.

A computer readable medium comprising instructions that, when executed, cause a device to receive a first evoked compound action potential (ECAP) signal elicited by a first polarity configuration of stimulus electrodes and receive a second ECAP signal elicited by a second polarity configuration of the stimulus electrodes opposite the first polarity configuration. The instructions also cause the device to generate an adjusted second ECAP signal by temporally aligning at least a portion of the second ECAP signal to at least a portion of the first ECAP signal, and generate a composite ECAP signal based on the first ECAP signal and the adjusted second ECAP signal. Additionally, the instructions cause the device to output the composite ECAP signal.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

configured to deliver spinal cord stimulation (SCS) therapy and an external programmer, in accordance with one or more techniques of this disclosure.

Figure 2:
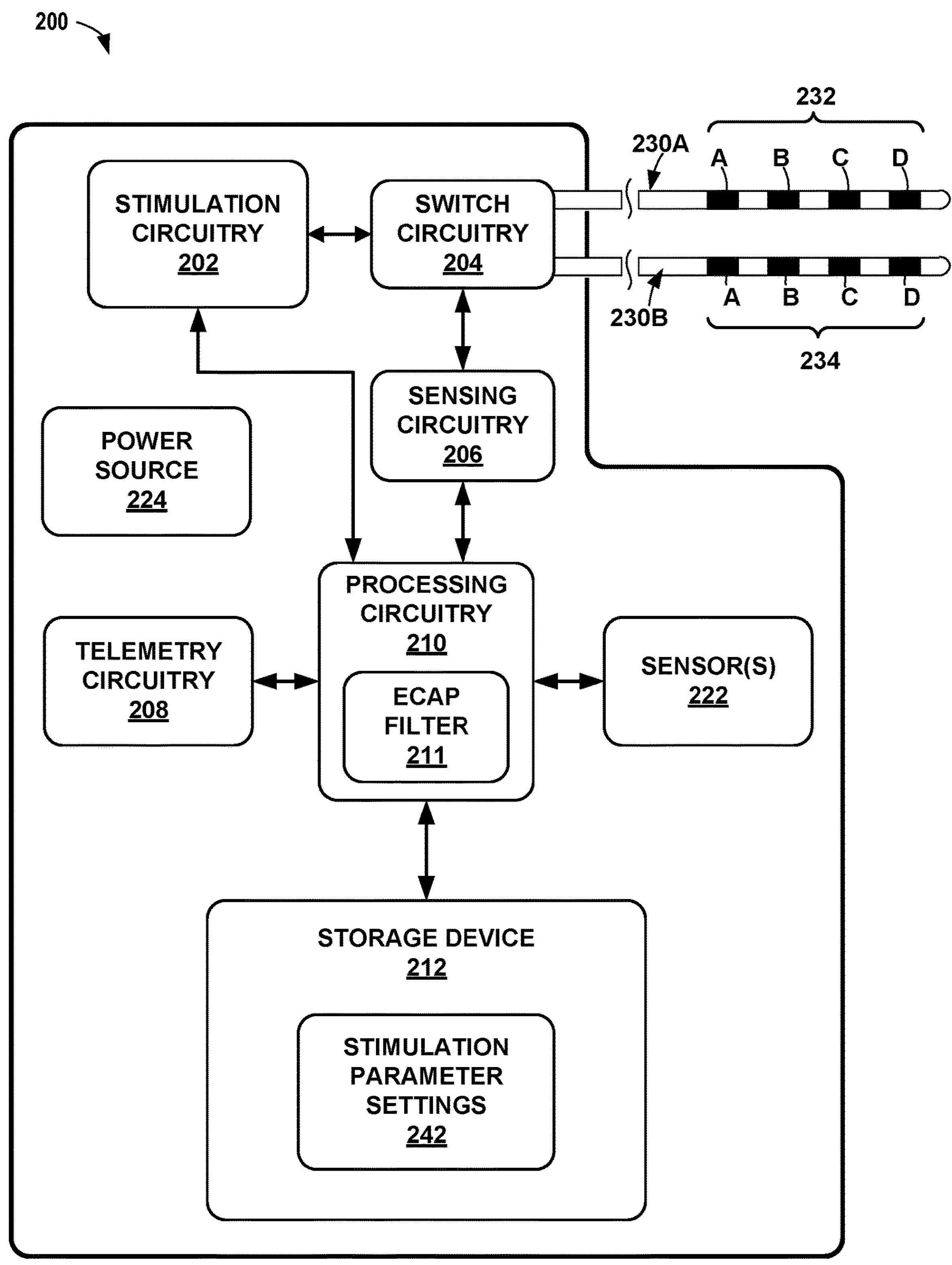

FIG. 2 is a block diagram illustrating an example configuration of components of an implantable medical device (IMD), in accordance with one or more techniques of this disclosure.

Figure 3:
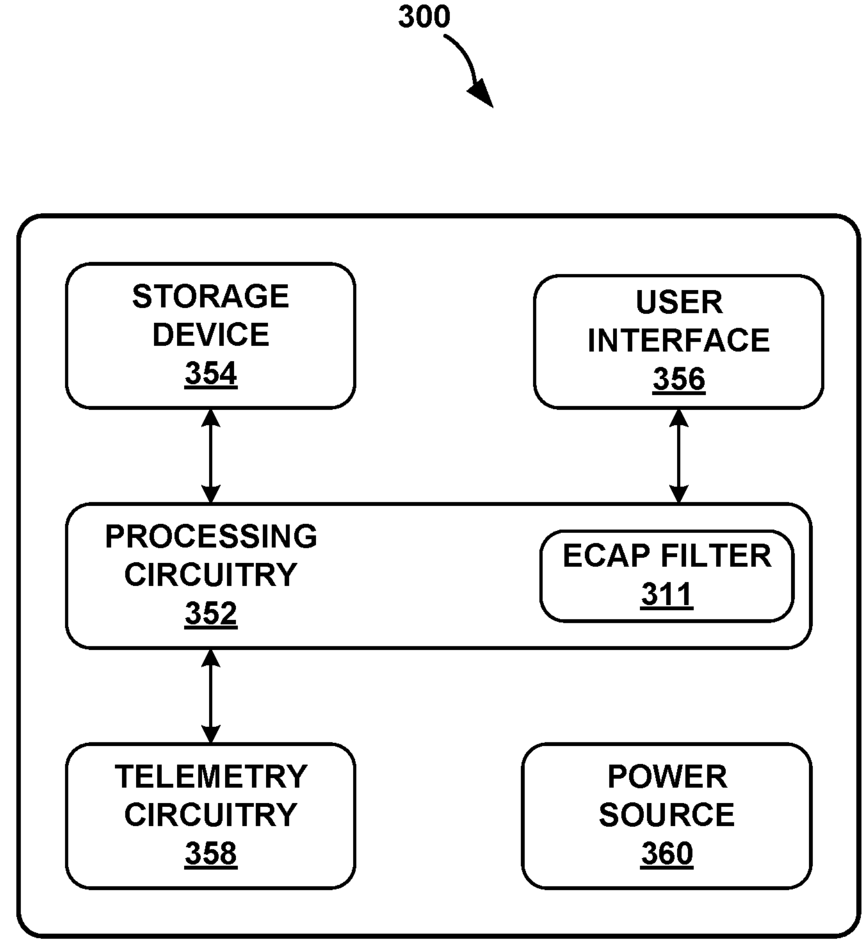

FIG. 3 is a block diagram illustrating an example configuration of components of an example external programmer, in accordance with one or more techniques of this disclosure.

Figure 4:
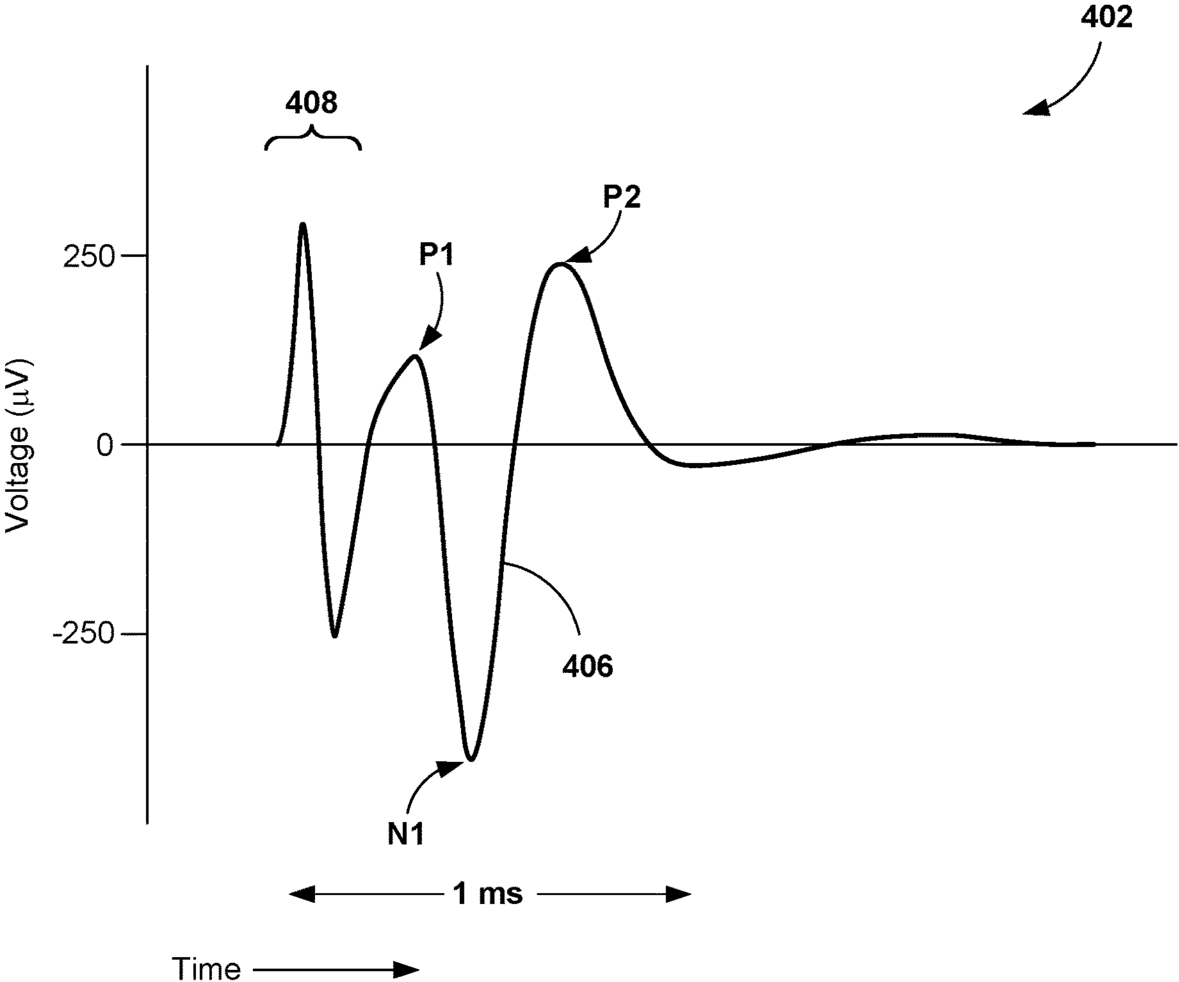

FIG. 4 is a graph of example evoked compound action potentials (ECAPs) sensed for respective stimulation pulses, in accordance with one or more techniques of this disclosure.

Figure 5A:
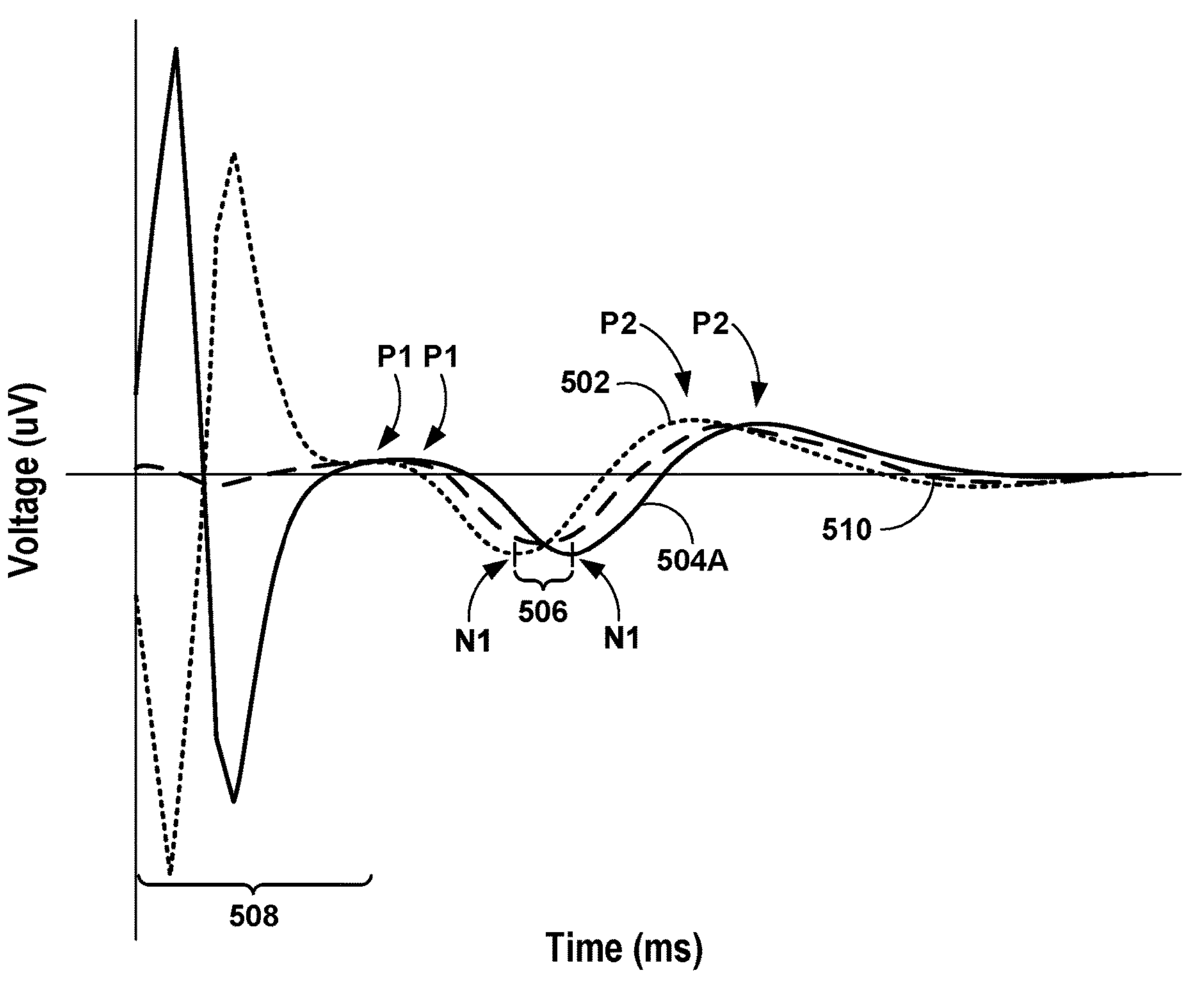
Figure 5B:
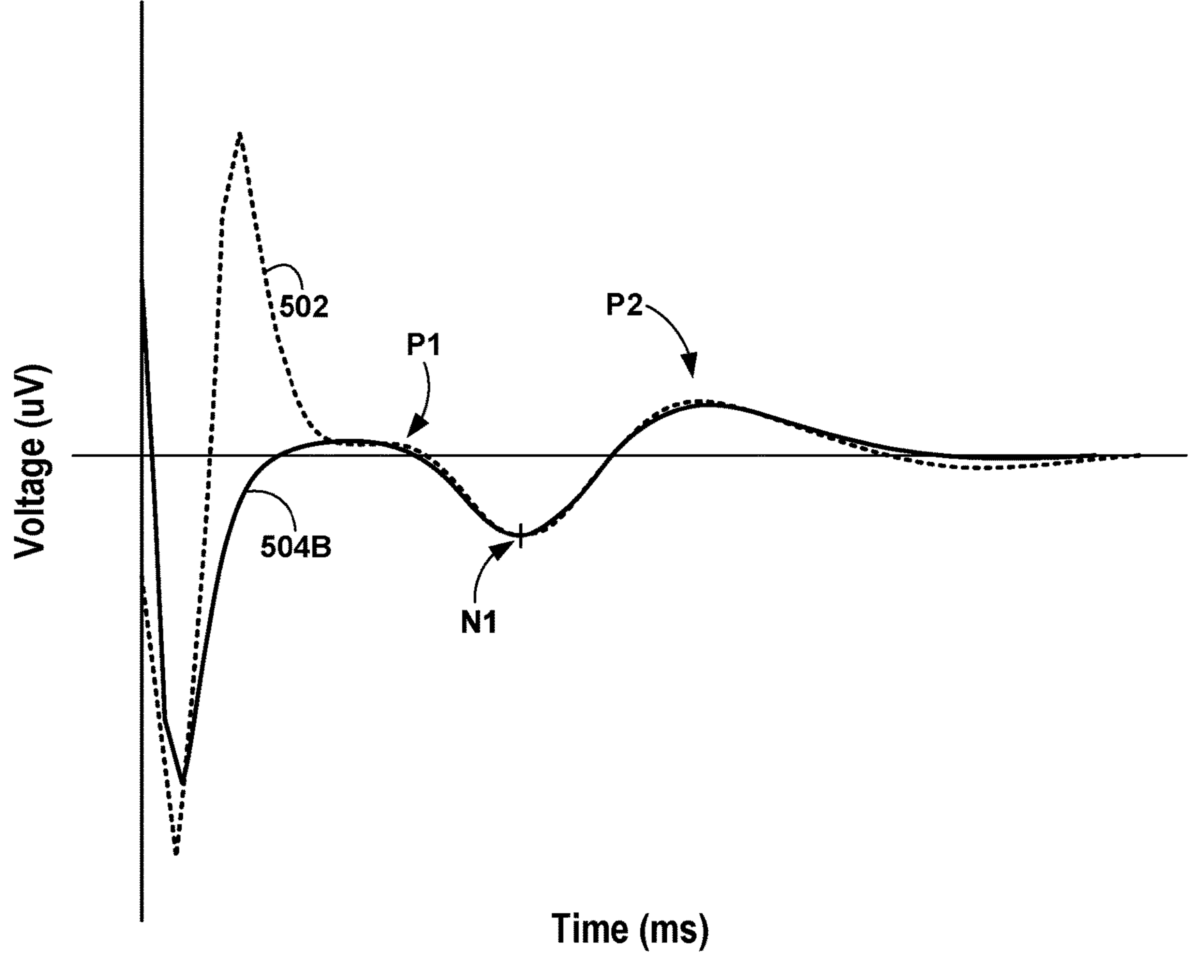
Figure 5C:
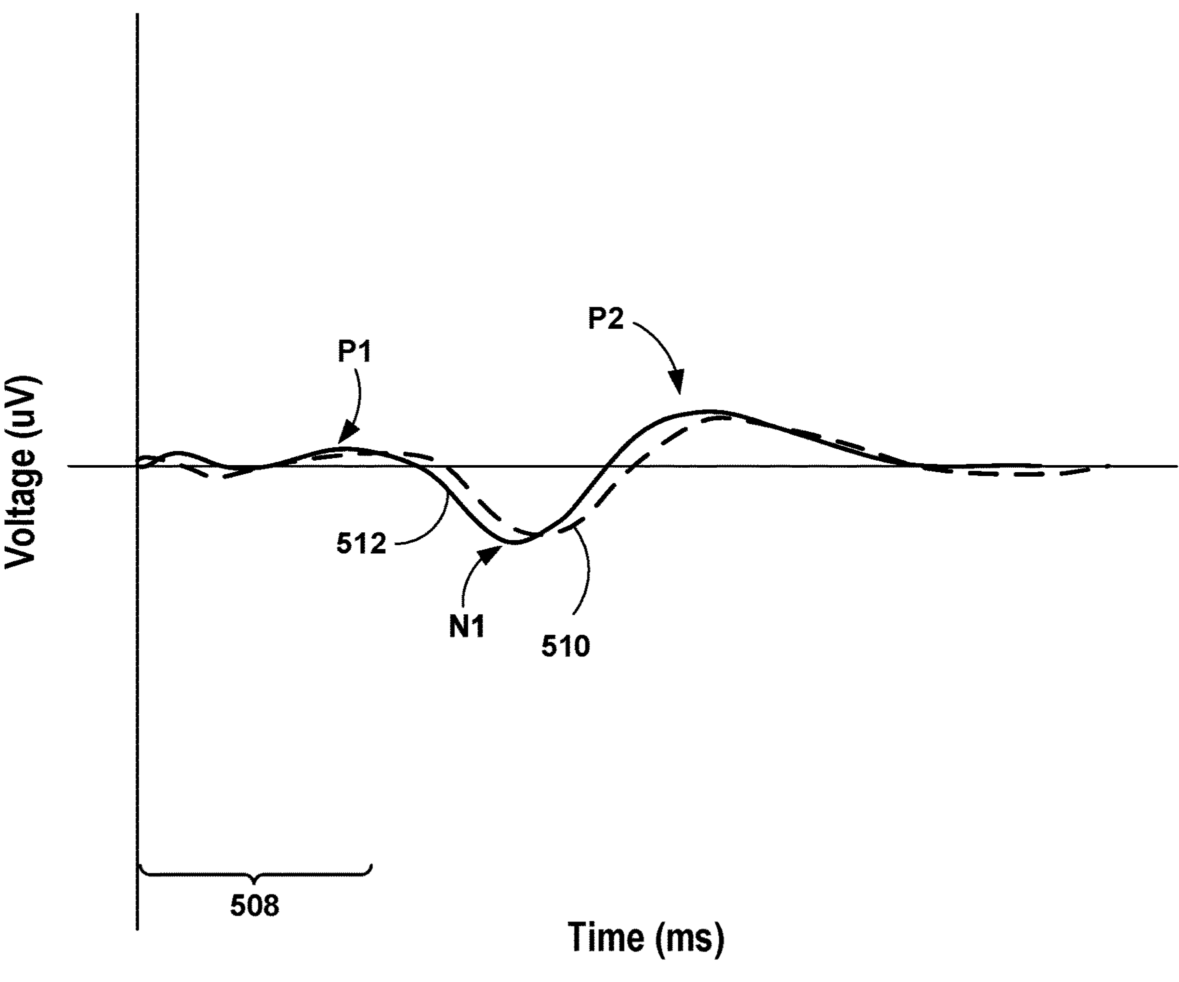

FIGS. 5A, 5B, and 5C illustrate ECAPs being aligned in accordance with one or more techniques of this disclosure.

Figure 6:
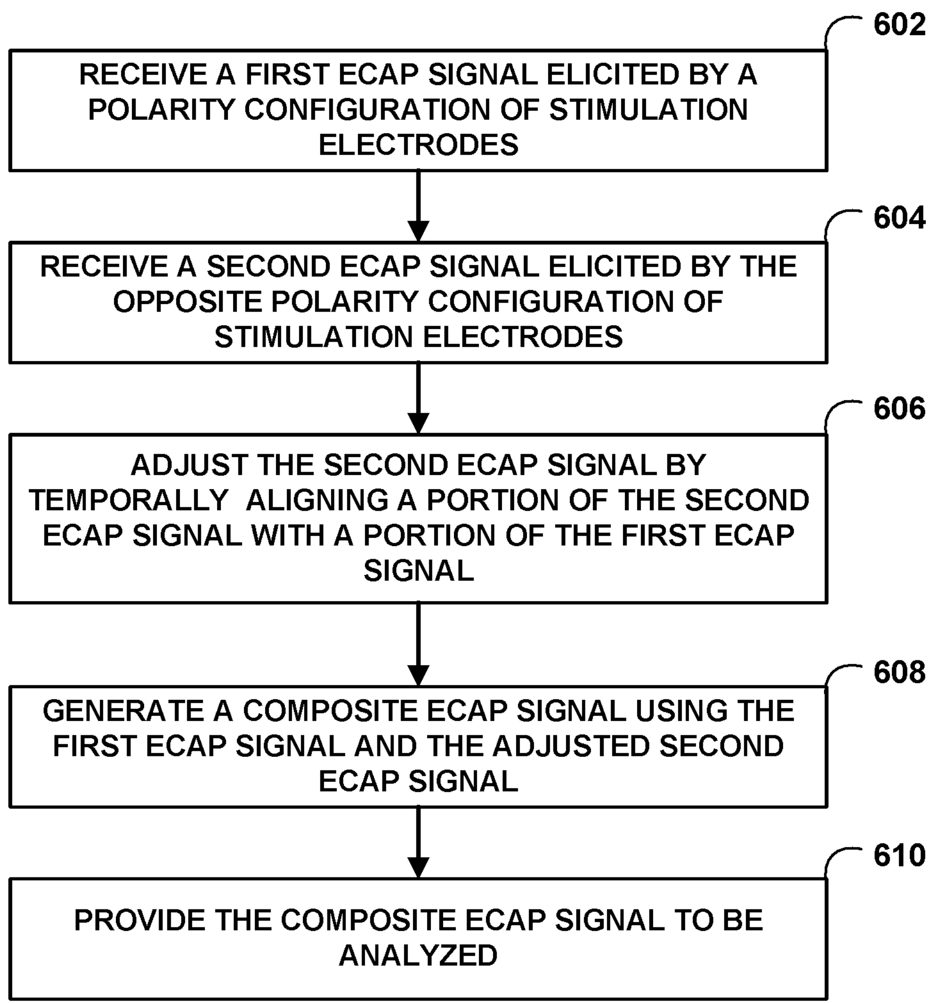

FIG. 6 is a flowchart of an example method to align ECAPs in accordance with one or more techniques of this disclosure.

DETAILED DESCRIPTION

The disclosure describes examples of medical devices, systems, and techniques to correct phase misalignment of evoked compound action potential (ECAP) measurements from alternating polarity stimulus. Alternating polarity stimulus can be used to cancel stimulation artifacts or improve signal amplitude (e.g., increase signal to noise ratios) when sensing ECAPs. Using a bi-polar electrode combination of two or more electrodes, alternating polarity stimulus use a combination of electrodes, where one electrode is a cathode and the other electrode is an anode for a first stimulus (sometimes referred to as the "'A' Pulse") and where the polarity of the two electrodes are switched for a second stimulus (sometimes referred to as the "'B' Pulse"). A second set of electrodes is used to sense the resulting ECAPs. Because neural stimulation is initiated at the cathode, alternating the cathode from the two different electrode combination polarities may change a distance between the stimulus at the sensing electrodes, for example, in systems where the electrodes are along the same axis or generally parallel axes (e.g., as opposed to system where the stimulus electrodes are perpendicular to the sensing electrodes, etc.). This may cause the timing of the first ECAP signal to be offset compared to the second ECAP signal. For example, if (i) a stimulation lead is lying in the epidural space parallel to the tracts of the dorsal columns and has electrodes on a 9 mm pitch, (ii) the conduction velocity is 100 m/s, and (iii) the action potential is launched on the leading edge of the first pulse of the stimulus complex, the first ECAP signal may arrive at the sensing electrodes in 540 μs and the second ECAP potential may arrive at the sensing electrode in 450 μs.

Typically, the two ECAPs are averaged together to remove artifacts from the signal and/or improve the overall amplitude of the signal. For example, a closer cathode may result in a larger sensed ECAP signal, but the closer cathode may also cause more stimulation artifact in the sensed ECAP signal. Conversely, the farther cathode may produce less of a stimulation artifact and a slightly lower amplitude of the ECAP signals. Averaging these ECAP signals may provide an improved overall signal to noise ratio along with first-order cancelation of the stimulation artifact as the polarity of the artifact flips between the "A" and "B" pulses but the ECAP polarity does not. However, directly averaging these two sensed ECAP signals results in an amplitude less than the individual ECAPs as elicited from the raw stimulation because of the timing misalignment (e.g., the peaks of the ECAP signals are out of phase). Thus, averaging the two ECAP signals without any adjustment may result in a loss of signal amplitude, which can be difficult to further analyze when the signals are relatively small in amplitude and a maximal signal-to-noise ratio is preferred. This issue may not occur in other configurations of leads in which the sensing electrodes are located between the stimulus electrons (e.g., in a "T" formation, etc.). However, leads lying along the spinal cord or a peripheral nerve often include a parallel electrodes.

As described below, processing circuitry characterizes the misalignment between the two ECAP signals. The processing circuitry may characterize the misalignment in one or more ways. For examples, processing circuitry may include a trough or peak detector that determines an amount of temporal offset between a common feature of the ECAPs elicited from the "A" pulse and "B" pulse. As another examples, the processing circuitry may determine the misalignment by dividing the conduction velocity into the electrode spacing to calculate the amount of shift. In some examples, stimulation circuitry of an IMD may be controlled so that the sensing electrode combination changes to compensate for the change in the location of the cathode of the "B" pulse to minimize a temporal effect. In such examples, the processing circuitry may then characterize the misalignment as described herein. The processing circuitry compensates for the misalignment by processing one or both ECAPs to adjust the timing characteristics such that the two ECAP signals are temporally aligned. The processing circuitry averages the two ECAP signals to generate a composite ECAP signal or a portion thereof for further analysis, such as determining an effectiveness of stimulation, determining a placement a lead associated with the electrodes, migration of a lead associated with the electrodes, and/or posture of the patient, etc. The processing circuitry may be part of an implantable medical device (IMD), an external programmer, or a remote server (e.g., a cloud server, etc.). This provides for an accurate ECAP signal measurement with artifact filtering without substantially reducing an amplitude of the resultant composite ECAP compared to the two sensed ECAP signals.

Figure 1:
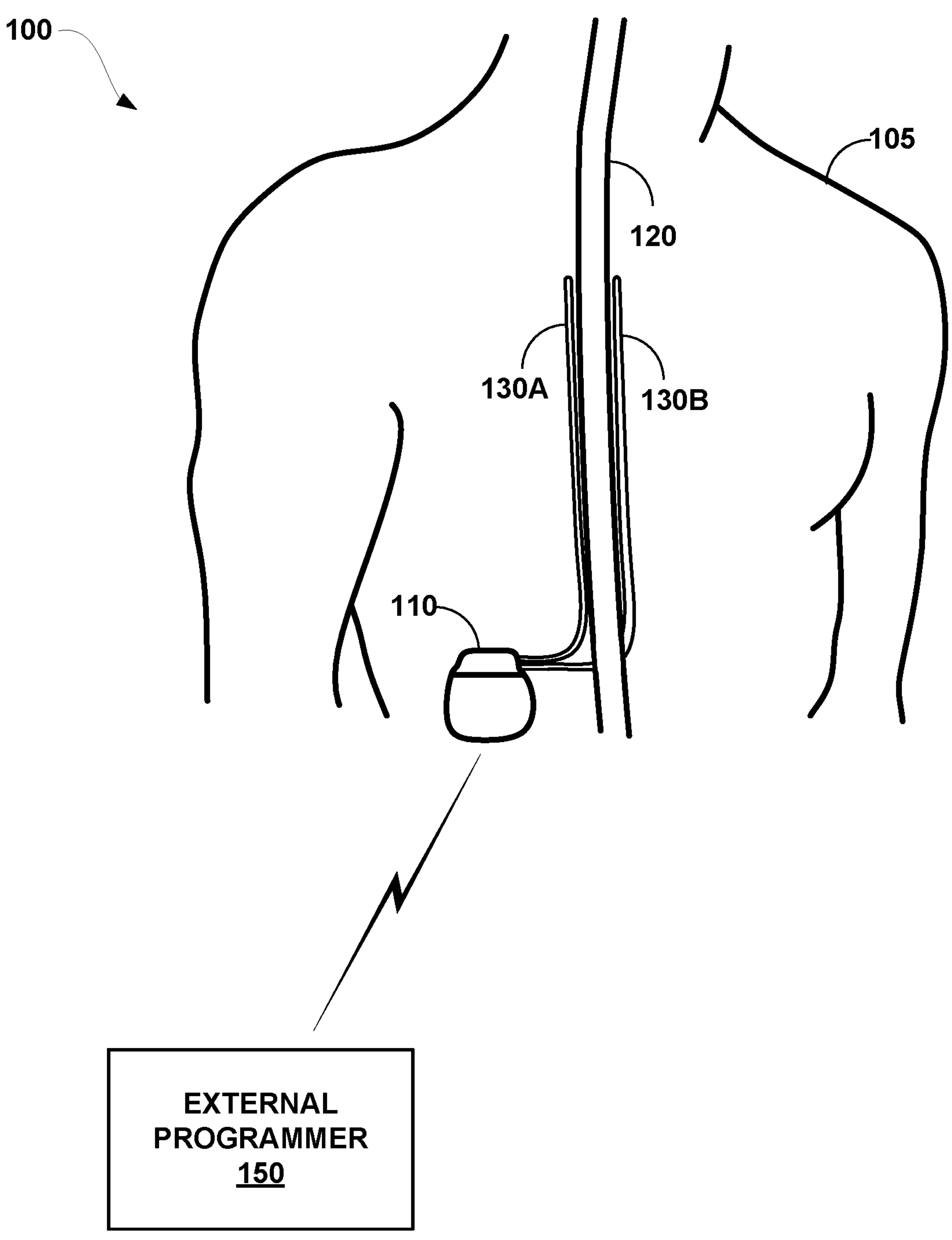
FIG. 1 is a conceptual diagram illustrating an example system that includes an implantable medical device (IMD)

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in the example of FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to detect whether leads 130 have migrated from their implanted location. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

In some examples, IMD 110 may determine an ECAP value based on multiple ECAP signals elicited by respective different electrical stimuli. IMD 110 may deliver each stimulus using a bipolar electrode configuration (sometimes referred to as a "stimulus electrode combination") and sense the resulting ECAP signal with multiple sensing electrodes (sometimes referred to as a "sensing electrode combination"). The IMD 110 delivers the first stimulation pulse ("A" Pulse) using a first stimulus electrode as the cathode and a second stimulus electrode as the anode. The "A" Pulse is sensed by a sensing electrode combination. The IMD 110 delivers the second stimulus ("B" Pulse), switching the stimulus electrodes such that the second stimulus electrode is the cathode and the first stimulus electrode is the anode. In some examples, the IMD 110 may change which sensing electrode combination (e.g., which electrodes and/or polarities of the electrode combination) is used to sense the "B" Pulse to compensate to the changed location of the stimulus electrode being used as the cathode. While described herein as using two electrodes (e.g., one anode and one cathode, etc.), the pulses may be generated with more that two electrodes (e.g., two anodes and two cathodes, etc.).

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced adjacent to spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which causes a tingling sensation that may reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation. For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information, such as the "A" Pulse and "B" Pulse ECAP signals, may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In some examples, IMD 110 analyzes the "A" Pulse and the "B" Pulse ECAP signals to generate a composite ECAP signal or a portion thereof. Alternatively or additionally, in some examples, external programmer 150 may analyzes the "A" Pulse and the "B" Pulse ECAP signals to generate the composite ECAP signal. In other examples, the "A" Pulse and the "B" Pulse ECAP signals may be sent (e.g., via external programmer 150) to a remote server to generate the composite ECAP signal.

IMD 110 characterizes the misalignment between the "A" Pulse and the "B" Pulse ECAP signals by, for examples, using a trough or peak detector to determine an amount of temporal offset between a common feature of the "A" Pulse and the "B" Pulse ECAP signals. As another examples, IMD 110 divides the conduction velocity (e.g., stored in memory, etc.) into the electrode spacing (e.g., stored in memory, etc.) to estimate the expected amount of temporal shift between the "A" Pulse ECAP signal and the "B" Pulse ECAP signal. For example, IMD 110 may determine that the temporal shift is 90 microseconds (μs). IMD 110 compensates for the misalignment by processing one or both the ECAPs signal to adjust the timing characteristics such that the two ECAP signals are temporally aligned. For example, IMD 100 may adjust the "B" Pulse ECAP signal by 90 μs. IMD 110 can then average the magnitudes of the "A" Pulse and the "B" Pulse ECAP signals to generate the composite ECAP signal.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores stimulation parameter settings 242 in separate memories within storage device 212 or separate areas within storage device 212. In some examples, stimulation parameter settings 242 may include stimulation parameter values (sometimes referred to as "sets of therapy parameters") for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulus electrode combination, electrode polarity, current or voltage amplitude, pulse width, pulse rate, and pulse shape. In some examples, stimulation parameter settings 242 may store a primary set of therapy parameters for when leads 230 are in an implant location and a secondary set of therapy parameters for when one of leads 230 have migrated. Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulus electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. At least a pair of electrodes 232 and 234 on each of leads 230A and 230B are used to provide a stimulus to provoke an "A" Pulse ECAP and a "B" Pulse ECAP. In some examples, the one or more of the electrodes are bipolar electrodes. Generally, the bipolar electrode combination uses electrodes carried by the same lead. For example, to provoke the "A" Pulse ECAP, electrode 232C may act as a cathode and electrode 232D may act as an anode. For example, to provoke the "B" Pulse ECAP, electrode 232D may act as a cathode and electrode 232C may act as an anode. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the illustrated example, processing circuitry 210 includes an ECAP filter 211 to generate a composite ECAP signal. ECAP filter 211 characterizes the misalignment of the "A" Pulse ECAP signal and the "B" Pulse ECAP signal as described herein. ECAP filter 211 temporally aligns the "A" Pulse ECAP signal and the "B" Pulse ECAP signal. The ECAP filter 211 then averages the "A" Pulse ECAP signal and the "B" Pulse ECAP signal to generate the composite ECAP signal.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. One or more of electrodes 232 and 234 are suitable for sensing the ECAPs. For example, electrodes 232A and 234A may be used to sense the ECAPs, while electrodes 232C, 232D, 234C, and 234D are used to provide stimulation. In some examples, either electrodes 232A and 234A or electrodes 232B and 234B may be used to sense the ECAP depending on the polarity configuration of electrodes 232C, 232D, 234C, and 234D when delivering the stimulation to provoke the ECAP. For example, electrode 232A may be used to sense the ECAP when electrode electrodes 232C is acting as a cathode, and electrode 232B may be used to sense the ECAP when electrode electrodes 232D is acting as the cathode.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store stimulation parameter settings 242.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, such as a representation of the baseline ECAP signal, a representation of the most recent captured ECAP signal, a measure of the latency between stimulation and ECAP detection, and/or an alert indicative of the migration state of leads 130. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation. During the calibration process of obtaining ECAP signals for different posture states, user interface 356 may present the posture state that the patient should assume, and user interface 356 may receive user input confirming that the patient is in the requested posture state. The calibration process may also incorporate radiographic data such as x-rays, fluorographs, CT scans, MR images or the like, and relate those data to the ECAP signal. In other examples, user interface 356 may receive user input indicating the posture state that the patient is in and generate the relationship of the detected ECAP characteristic values obtained during the calibration (e.g., the calibrated growth curve) for that indicated posture state.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs in response to an indication that the leads have migrated. For example, user interface 356 may receive an indication from the clinician to adjust a pulse width and/or an amplitude of the stimulation parameter values to compensate for the migration of the leads. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

External programmer 150 can perform the signal analysis and other functions described with respect to IMD 200 or any other device herein. In one example, external programmer 150 receives the "A" Pulse ECAP signal and the "B" Pulse ECAP signal from IMD 110. External programmer 150 may include an ECAP filter 311 to generate a composite ECAP signal. ECAP filter 311 characterizes the misalignment of the "A" Pulse ECAP signal and the "B" Pulse ECAP signal as described herein. ECAP filter 311 temporally aligns the "A" Pulse ECAP signal and the "B" Pulse ECAP signal. The ECAP filter 311 then averages the "A" Pulse ECAP signal and the "B" Pulse ECAP signal to generate the composite ECAP signal.

FIG. 4 is a graph 402 of example evoked compound action potentials (ECAPs) sensed for respective stimulation pulses, in accordance with one or more techniques of this disclosure. Peaks 408 of ECAP signal 406 are detected and represent the artifact of the delivered control pulse. After peaks 408, ECAP signal 406 also includes peaks P1, N1 (sometime referred to as a valley), and P2, which are three typical peaks representative of propagating action potentials from an ECAP. Peaks P1, N1 and/or P2 may be features used to temporally align two ECAPs. In the illustrated example, duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact, a relatively large signal, impinges on P1. Additionally, the N1-P2 amplitude may be minimally affected by electronic drift in the signal. In other examples, the characteristic of the ECAP used to detect the posture state of the patient and/or control informed pulses may be an amplitude of P1, N1, or P2 with respect to neutral or zero voltage. In some examples, the characteristic of the ECAP may be a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two or more points in the ECAP signal, such as the slope between N1 and P2. For example, the characteristic may include the difference between two slopes (i.e. slope from N1 to P2 and the slope from P2 to end, etc.). In other examples, the characteristic of the ECAP may be the time between two points of the ECAP, such as the time between N1 and P2. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples. The amplitude of the ECAP signal generally increases with increased amplitude of the control pulse, as long as the pulse amplitude is greater than threshold such that nerves depolarize and propagate the signal.

FIGS. 5A, 5B, and 5C illustrate ECAPs being aligned in accordance with one or more techniques of this disclosure. FIG. 5A illustrates an "A" Pulse ECAP signal 502, a "B" Pulse ECAP signal 504A. "A" Pulse ECAP signal 502 and "B" Pulse ECAP signal 504A are out of sync (e.g., out of phase) by the amount of time indicated by delay 506. In the illustrated example, delay 506 is measured as the difference between peak N1 of "A" Pulse ECAP signal 502 and peak N1 of "B" Pulse ECAP signal 504A. FIG. 5A also illustrates an artifact period 508 in which an artifact is present in "A" Pulse ECAP signal 502. Artifact period 508 includes the sensed stimuli that elicited each ECAP signal. Note that the polarities of the stimuli are reversed, or opposite, from each other, but that the resulting peaks in the ECAP signals have the same polarity. For exemplary purposes, FIG. 5A also illustrates an average ECAP signal 510 generated without first synchronizing "A" Pulse ECAP signal 502 and "B" Pulse ECAP signal 504. In the illustrated example, because "A" Pulse ECAP signal 502 and "B" Pulse ECAP signal 504 are out of sync by delay 508, average ECAP signal 506.

The example of FIG. 5B illustrates a time-shifted "B" Pulse ECAP signal 504B. "B" Pulse ECAP signal 504B is shifted (e.g., moved forward in time) to align with "A" Pulse ECAP signal 502. In the illustrated examples, peak N1 of "A" Pulse ECAP signal 502 is aligned with peak N1 of "B" Pulse ECAP signal 504B. As a result of the alignment of the "A" Pulse ECAP signal 502 with the "B" Pulse ECAP signal 504B, the system can calculate an average of the ECAP signals 502 and 504B that improves the accuracy of the ECAP amplitudes as compared with the non-adjusted "B" Pulse ECAP signal 504A.

The example of FIG. 5C illustrates a composite ECAP signal 512. Composite ECAP signal 512 is based on an average of "A" Pulse ECAP signal 502 and time shifted "B" Pulse ECAP signal 504 of FIG. 5B. As compared to average ECAP signal 510, composite ECAP signal 512 retains a greater peak-to-peak amplitude (e.g., the amplitude between peak N1 and peak P2, etc.) and timing characteristics which facilitate detecting a change in the ECAP signal indicative of, for example, a change in the stimulation, a change in position of the lead, a change in posture of the patient, etc. In some examples, the ECAP filter may smooth a portion of the composite ECAP signal that is associated with artifact period 508 of "A" Pulse ECAP signal 502.

FIG. 6 is a flowchart of an example method to align ECAPs in accordance with one or more techniques of this disclosure. Initially, processing circuitry 210 receives a first ECAP signal (e.g., "A" Pulse ECAP signal 502) from sensing circuitry 206 elicited by a polarity configuration of stimulus electrodes (602). In some examples, the processing circuitry may be executing the ECAP filter (e.g., ECAP filter 211, ECAP filter 311, etc.). Processing circuitry 210 also receives a second ECAP signal (e.g., "B" Pulse ECAP signal 504A) from sensing circuitry 206 elicited by the opposite polarity configuration of the stimulus electrodes (604). The stimuli of alternating polarities can be delivered in any order and their respective ECAP signals received. Processing circuitry 210 filter adjusts the second ECAP signal by temporally aligning a portion of the second ECAP signal (e.g., "B" Pulse ECAP signal 504B) with a portion of the first ECAP signal (606). For example, Processing circuitry 210 may perform peak detection to align a particular peak (e.g., P1, N1, or P2, etc.) of the first ECAP signal with the same peak of the second ECAP signal. Processing circuitry 210 then generates a composite ECAP signal using the first ECAP signal and the adjusted second ECAP signal (608). Processing circuitry 210 then provides the composite ECAP signal to be further analyzed (610).

Processing circuitry 210 may determine a characteristic value of the composite ECAP signal and utilize the characteristic value of the composite ECAP signal as feedback that informs one or more aspects of electrical stimulation, such as intensity of subsequent electrical stimulation therapy. For example, processing circuitry 210 may adjust one or more parameter values that define subsequent electrical stimulation based on the characteristic value. Example parameter values that may be adjusted may include current amplitude, pulse width, and/or frequency of delivered pulses. Processing circuitry 210 may monitor the characteristic values from respective composite ECAP signals over time and increase or decrease parameter values in order to maintain a target characteristic value or range of values as detected in the composite ECAP signals. In another example, processing circuitry 210 may monitor the characteristic values from composite ECAP signals over time and reduce a stimulation parameter value when the characteristic value exceeds a threshold in order to reduce the likelihood of overstimulation as perceived by the patient. Processing circuitry 210 may employ these or other control policies based on the determined characteristic value from determined composite ECAP signals as described herein.

Examples are set forth below.

Example 1A. An example system includes processing circuitry to receive a first evoked compound action potential (ECAP) signal elicited by a first polarity configuration of stimulus electrodes, and receive a second ECAP signal elicited by a second polarity configuration of the stimulus electrodes opposite the first polarity configuration. Additionally, the processing circuitry generates an adjusted second ECAP signal by temporally aligning at least a portion of the second ECAP signal to at least a portion of the first ECAP signal and generate at least a portion of a composite ECAP signal based on the first ECAP signal and the adjusted second ECAP signal. The processing circuitry also outputs at least the portion of the composite ECAP signal.

Example 1B. The system of Example 1A, wherein the processing circuitry characterizes a misalignment of the first ECAP signal and the second ECAP signal, and wherein the processing circuitry is configured to generate the adjusted the second ECAP signal by temporally aligning, based on the misalignment.

Example 1C. The system of Example 1A, wherein the processing circuitry generates the adjusted the second ECAP signal by temporally aligning an entire second ECAP signal by shifting the entire second ECAP signal by an amount of time.

Example 1D. The system of Example 1C, wherein the processing circuitry determines the amount of time by comparing a first time of a feature of the first ECAP signal to a second time of a corresponding feature of the second ECAP signal.

Example 1E. The system of Example 1C, wherein the processing circuitry determines the amount of time based on a conduction velocity of at least one nerve and a distance between the stimulus electrodes.

Example 1F. The system of Example 1E, wherein the conduction velocity is a patient specific conduction velocity for the at least one nerve.

Example 1G. The system of Example 1E, wherein the conduction velocity is a human average conduction velocity for the at least one nerve.

Example 1H. The system of any of Examples 1A through 1G, further including sensing circuitry to sense the first ECAP signal and second ECAP signal with at least one sensing electrode combination, and an implantable medical device that houses the processing circuitry and the sensing circuitry.

Example 1I. The system of Example 1H, wherein the sensing circuitry senses the first ECAP signal via a first sensing electrode combination and senses the second ECAP signal via a second sensing electrode different than the first sensing electrode to compensate for a distance between the stimulus electrodes.

Example 1J. The system of any of Examples 1A through 1I, wherein the processing circuitry determines a characteristics value from the composite ECAP signal, and adjusts at least one parameter of a plurality stimulation parameters that define a stimulus to provide therapy.

Example 2A. An example method comprising including receiving, by processing circuitry, a first evoked compound action potential (ECAP) signal elicited by a first polarity configuration of stimulus electrodes, and receiving a second ECAP signal elicited by a second polarity configuration of the stimulus electrodes opposite the first polarity configuration. The example method also includes generating an adjusted second ECAP signal by temporally aligning at least a portion of the second ECAP signal to at least a portion of the first ECAP signal, and generating a composite ECAP signal based on the first ECAP signal and the adjusted second ECAP signal. Additionally, the example method includes outputting at least a portion of the composite ECAP signal.

Example 2B. The method of Example 1A, including characterizing a misalignment of the first ECAP signal and the second ECAP signal, and wherein generating the adjusted the second ECAP signal include temporally aligning, based on the misalignment.

Example 2C. The method of Example 1A, wherein generating the adjusted the second ECAP signal includes temporally aligning an entire second ECAP signal by shifting the entire second ECAP signal by an amount of time.

Example 2D. The method of Example 2C, including determine the amount of time by comparing a first time of a feature of the first ECAP signal to a second time of a corresponding feature of the second ECAP signal.

Example 2E. The method of Example 2C, including determining the amount of time based on a conduction velocity of at least one nerve and a distance between the stimulus electrodes.

Example 2F. The method of Example 2E, wherein the conduction velocity is a patient specific conduction velocity for the at least one nerve.

Example 2G. The method of Example 2E, wherein the conduction velocity is a human average conduction velocity for the at least one nerve.

Example 2H. The method of any of Examples 2A through 2G, including sensing the first ECAP signal via a first sensing electrode combination, and sensing the second ECAP signal via a second sensing electrode different than the first sensing electrode to compensate for a distance between the stimulus electrodes.

Example 21. The method of any of Examples 2A through 2H, including determining a characteristics value from the composite ECAP signal, and adjusting at least one parameter of a plurality stimulation parameters that define a stimulus to provide therapy.

Example 3. An example computer readable medium comprising instructions that, when executed, cause a device to receive a first evoked compound action potential (ECAP) signal elicited by a first polarity configuration of stimulus electrodes, and receive a second ECAP signal elicited by a second polarity configuration of the stimulus electrodes opposite the first polarity configuration. The instructions cause the device to generate an adjusted second ECAP signal by temporally aligning at least a portion of the second ECAP signal to at least a portion of the first ECAP signal, and generate a composite ECAP signal based on the first ECAP signal and the adjusted second ECAP signal. Additionally, the instructions cause the device to output at least a portion of the composite ECAP signal.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:

stimulation circuitry configured deliver electrical stimulation therapy via one or more stimulus electrodes;

processing circuitry configured to:

receive a first evoked compound action potential (ECAP) signal elicited by a first stimulus generated from a first polarity configuration of the stimulus electrodes;

receive a second ECAP signal elicited by a second stimulus generated from a second polarity configuration of the stimulus electrodes opposite the first polarity configuration;

generate an adjusted second ECAP signal by temporally aligning at least one of a P1, N1, or P2 peak of the second ECAP signal to at least one of a corresponding P1, N1, or P2 peak of the first ECAP signal;

generate at least a portion of a composite ECAP signal based on the first ECAP signal and the adjusted second ECAP signal; and control, based on the portion of the composite ECAP signal, the stimulation circuitry to deliver the electrical stimulation therapy via the one or more stimulus electrodes.

2. The system of claim 1, wherein the processing circuitry is configured to characterize a misalignment of the first ECAP signal and the second ECAP signal, and wherein the processing circuitry is configured to generate the adjusted second ECAP signal by temporally aligning, based on the misalignment.

3. The system of claim 1, wherein the processing circuitry is configured to generate the adjusted second ECAP signal by temporally aligning an entire second ECAP signal by shifting the entire second ECAP signal by an amount of time.

4. The system of claim 3, wherein the processing circuitry is configured to determine the amount of time by comparing a first time of a feature of the first ECAP signal to a second time of a corresponding feature of the second ECAP signal.

5. The system of claim 3, wherein the processing circuitry is configured to determine the amount of time based on a conduction velocity of at least one nerve and a distance between the stimulus electrodes.

6. The system of claim 5, wherein the conduction velocity is a patient specific conduction velocity for the at least one nerve.

7. The system of claim 5, wherein the conduction velocity is a human average conduction velocity for the at least one nerve.

8. The system of claim 1, further comprising:

sensing circuitry to sense the first ECAP signal and the second ECAP signal with at least one sensing electrode combination; and an implantable medical device that houses the processing circuitry and the sensing circuitry.

9. The system of claim 8, wherein the sensing circuitry is configured to sense the first ECAP signal via a first sensing electrode combination and to sense the second ECAP signal via a second sensing electrode combination different than the first sensing electrode combination to compensate for a distance between the stimulus electrodes.

10. The system of claim 1, wherein the processing circuitry is configured to control delivery of electrical stimulation therapy by at least:

determining a characteristic value from at least the portion of the composite ECAP signal; and adjusting at least one parameter of a plurality stimulation parameters that define the electrical stimulation therapy to be delivered by the stimulation circuitry.

11. A method comprising:

receiving, by processing circuitry, a first evoked compound action potential (ECAP) signal elicited by a first polarity configuration of one or more stimulus electrodes;

receiving a second ECAP signal elicited by a second polarity configuration of the stimulus electrodes opposite the first polarity configuration;

generating an adjusted second ECAP signal by temporally aligning at least one of a P1, N1, or P2 peak of the second ECAP signal to at least one of a corresponding P1, N1, or P2 peak of the first ECAP signal;

generating a composite ECAP signal based on the first ECAP signal and the adjusted second ECAP signal; and controlling, by the processing circuitry and based on the portion of the composite ECAP signal, stimulation circuitry to deliver the electrical stimulation therapy via the one or more stimulus electrodes.

12. The method of claim 11, comprising characterizing a misalignment of the first ECAP signal and the second ECAP signal, and wherein generating the adjusted second ECAP signal include temporally aligning, based on the misalignment.

13. The method of claim 11, wherein generating the adjusted second ECAP signal includes temporally aligning an entire second ECAP signal by shifting the entire second ECAP signal by an amount of time.

14. The method of claim 13, comprising determine the amount of time by comparing a first time of a feature of the first ECAP signal to a second time of a corresponding feature of the second ECAP signal.

15. The method of claim 13, comprising determining the amount of time based on a conduction velocity of at least one nerve and a distance between the stimulus electrodes.

16. The method of claim 15, wherein the conduction velocity is a patient specific conduction velocity for the at least one nerve.

17. The method of claim 15, wherein the conduction velocity is a human average conduction velocity for the at least one nerve.

18. The method of claim 11, comprising:

sensing the first ECAP signal via a first sensing electrode combination; and sensing the second ECAP signal via a second sensing electrode different than the first sensing electrode to compensate for a distance between the stimulus electrodes.

19. The method of claim 11, wherein controlling the delivery of electrical stimulation therapy comprises:

determining a characteristic value from at least the portion of the composite ECAP signal; and adjusting at least one parameter of a plurality stimulation parameters that define the electrical stimulation therapy to be delivered by the stimulation circuitry.

20. A non-transitory computer readable medium comprising instructions that, when executed, cause processing circuitry to:

receive a first evoked compound action potential (ECAP) signal elicited by a first polarity configuration of one or more stimulus electrodes;

receive a second ECAP signal elicited by a second polarity configuration of the stimulus electrodes opposite the first polarity configuration;

generate an adjusted second ECAP signal by temporally aligning at least one of a P1, N1, or P2 peak of the second ECAP signal to at least one of a corresponding P1, N1, or P2 peak of the first ECAP signal;

generate a composite ECAP signal based on the first ECAP signal and the adjusted second ECAP signal; and control, based on the portion of the composite ECAP signal, stimulation circuitry to deliver the electrical stimulation therapy via the one or more stimulus electrodes.

* * * * *